United States Patent
Pierzynowski et al.

(10) Patent No.: US 7,759,396 B2
(45) Date of Patent: Jul. 20, 2010

(54) ANTINEOPLASTIC PREPARATION AND THE USE OF ANTINEOPLASTIC PREPARATION

(75) Inventors: Stefan Pierzynowski, Lund (SE); Martyna Kandefer-Szerszen, Lublin (PL); Wojciech Rzeski, Lublin (PL)

(73) Assignee: SGP & Sons AB, Lund (SE)

( * ) Notice: Subject to any disclaimer, the term of this patent is extended or adjusted under 35 U.S.C. 154(b) by 135 days.

(21) Appl. No.: 11/813,526

(22) PCT Filed: Jan. 10, 2006

(86) PCT No.: PCT/PL2006/000003

§ 371 (c)(1), (2), (4) Date: Oct. 23, 2007

(87) PCT Pub. No.: WO2006/075924

PCT Pub. Date: Jul. 20, 2006

(65) Prior Publication Data

US 2008/0058422 A1   Mar. 6, 2008

(30) Foreign Application Priority Data

Jan. 11, 2005   (PL) .................................... 372183

(51) Int. Cl.
*A61K 31/194* (2006.01)
*A61P 35/00* (2006.01)

(52) U.S. Cl. ..................................... 514/574

(58) Field of Classification Search .................. None
See application file for complete search history.

(56) References Cited

U.S. PATENT DOCUMENTS

| 5,006,551 | A | 4/1991 | Groke et al. |
| 6,429,229 | B1* | 8/2002 | Bouyssou et al. ........... 514/561 |
| 2004/0259766 | A1* | 12/2004 | Studzinski et al. ............. 514/2 |

FOREIGN PATENT DOCUMENTS

| WO | WO 2004/012662 | 2/2004 |
| WO | WO 2004/098619 A2 * | 11/2004 |
| WO | 2006/066244 | 6/2006 |

OTHER PUBLICATIONS

Robinson et al. Amino acid nutrition and immune function in tumour-bearing rats . . . Clinical Science. 1999, vol. 97, pp. 657-669.*

* cited by examiner

*Primary Examiner*—Jeffrey E Russel
(74) *Attorney, Agent, or Firm*—Ladas & Parry LLP

(57) ABSTRACT

A method for manufacturing an antineoplastic preparation containing alpha-ketoglutarate (AKG) or/and glutamine or/and glutamate or/and alpha-ketoglutarate of ornithine or/and dipeptides of glutamine and other amino acids or/and tripeptides of glutamine and other amino acids or/and di- and tripeptides of glutamate with other amino acid, or/and mono- and divalent metal salts and other of alpha-keto-glutarate or/and glutamine or/and glutamate or/and ornithine of alpha-ketoglutarate.

1 Claim, 7 Drawing Sheets

The proliferation of A549 cells with the stimulation by AKG

ANTINEOPLASTIC PREPARATION AND THE USE OF ANTINEOPLASTIC PREPARATION

SUMMARY OF THE INVENTION

An object of the invention is antineoplastic preparation and the use of antineoplastic preparation.

In spite of the significant progress in the chemotherapy, radiotherapy and immunotherapy in last years the problem of the effective antineoplastic therapy is still the serious challenge in a present medicine. Epidermiological research indicates that in countries fully developed one of three people suffers from the different neoplastic diseases. In that group each fourth case is a lethal one. Cytostatics actually used in treatment can have side effects thereby limiting the effectiveness and decreasing the quality of a patient's life.

Therefore the development of new drugs acting specifically on the neoplastic cells with the simultaneous protective activity on the normal cells is an especially urgent challenge.

The antineoplastic preparation distinguishes itself in that it contains alpha-ketoglutarate (AKG) or/and glutamine or/and glutamate or/and alpha-ketoglutarate of ornithine or/and dipeptides of glutamine and other amino acids or/and tripeptides of glutamine and other amino acids or/and di- and tripeptides of glutamate with other amino acid or/and mono- and divalent metal salts and other of alpha-keto-glutarate or/and glutamine or/and glutamate or/and ornithine of alpha-ketoglutarate.

The use of antineoplastic preparation is that the preparation containing alpha-ketoglutarate (AKG) or/and glutamine or/and glutamate or/and alpha-ketoglutarate of ornithine or and dipeptides of glutamine and other amino acids or/and tripeptides of glutamine and other amino acids or/and di- and tripeptides of glutamate with other amino acid or/and mono- and divalent metal salts and other of alpha-keto-glutarate or/and glutamine or/and glutamate or/and ornithine or alpha-ketoglutarate is used in the prophylaxis of neoplastic diseases.

Other use of antineoplastic preparation is that the preparation containing alpha-ketoglutarate (AKG) or/and glutamine or/and glutamate or/and alpha-ketoglutarate of ornithine or/and dipeptides of glutamine and other amino acids or/and tripeptides of glutamine and other amino acids or/and di- and tripeptides of glutamate with other amino acid or/and mono- and divalent metal salts and other of alpha-keto-glutarate or/and glutamine or/and glutamate or/and ornithine of alpha-keto-glutarate is used for metastases inhibition.

The preparation and the use of the preparation allows for the inhibition of the migration of neoplastic cells reflecting the potential role of AKG in the metastases inhibition. The preparation added to the diet plays a role as neo-adjuvant supporting existing methods used in the neoplasm treatment. It may improve the quality of the a patient's life through the synergistic action with antineoplastic drugs and simultaneous protective activity to normal cells.

The Cultures of Neoplastic Cells

Figure 1:
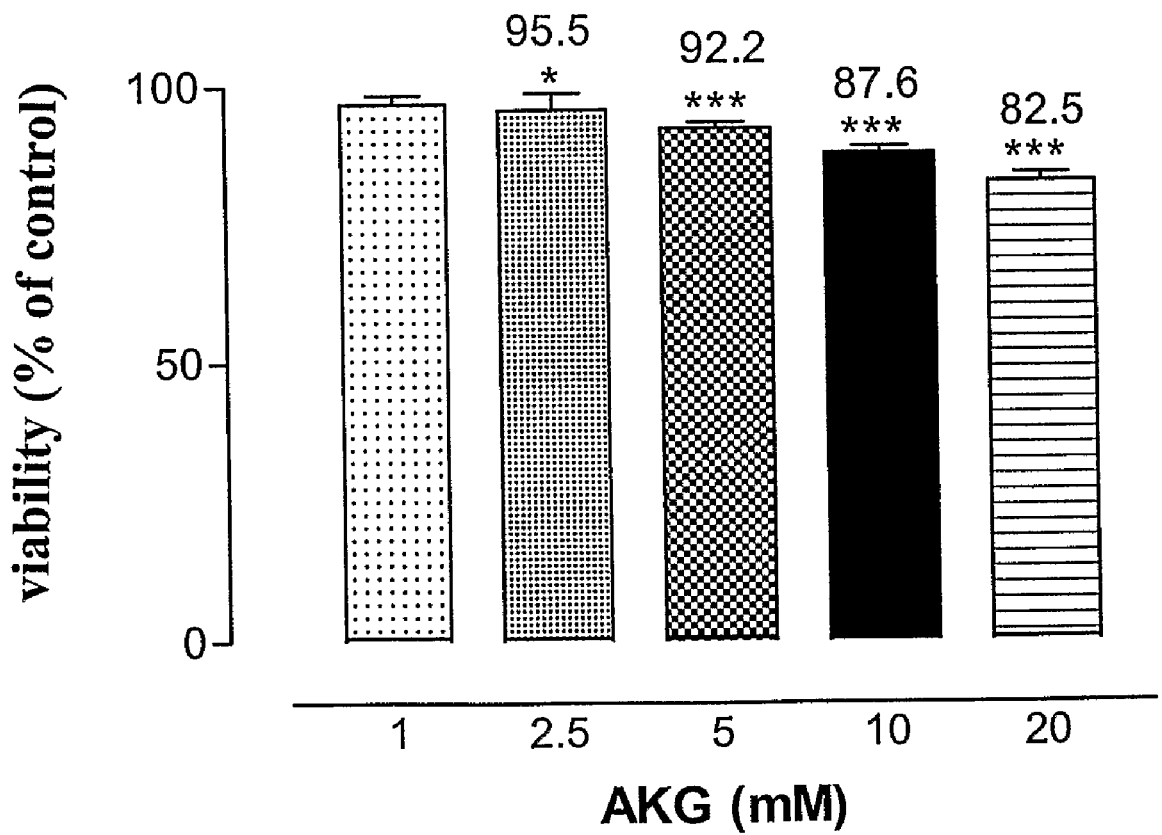
FIG. 1 depicts a curve presenting the proliferation of A549 cells with the stimulation by AKG.

A549—human neoplastic cells of the lung cancer; the continuous line obtained from the Institute of the Immunology and the Experimental Therapy of Polish Academy of Science in Wroclaw.

HT-29—human neoplastic cells of the large intestine cancer; the continuous line obtained from the Institute of the Immunology and the Experimental Therapy of Polish Academy of Science in Wroclaw.

C6—the rat neoplastic cells of the brain cancer (glioma); the continuous line obtained from the Department of Neonatology, Humboldt University, Berlin, Germany.

The Bases of the Culture

Cells of the A549 line were cultured on the basis DMEM: F-12 HAM (2:1), HT-29 and C6 cells on the basis DMEM. To the culture basis, 10% foetal beast serum (FBS), penicillin 100 i.u./ml and streptomycin 100 µg/ml were added. The basis DMEM:F-12 HAM, DMEM was produced by Sigma company (Sigma, St. Louis, Mo., U.S.A.). The foetal beast serum (FBS) was produced by Life Technologies company (Life Technologies, Karlsruhe, Germany). Remaining reagents were produced by Sigma company.

The Preparation of Cellular Cultures

Cells stored in liquid nitrogen in a tissue bank were unfrozen at a temperature of 37° C., then poured into the plastic bottles containing the proper basis. They were cultured in a temperature of 37° C. in the incubator with 5% $CO_2$ flow. After the cells' reproduction liquid was poured out, the cells were washed with PBS (without the calcium and magnesium ions) and processed with 0.25% trypsin solution+EDTA to receive the suspension of cells necessary in the experience.

Assessment of the Antiproliferative Activity of AKG in the Cellular Culture

Prepared earlier, in the culture basis, a suspension of cells with a density $1\times10^4$ cells/ml (A549), $4\times10^4$ cells/ml (HT-29) and $0.5\times10^4$ cells/ml (C6) was poured into the 96-pits microplate with the flat bottom (NUNC company, Roskilde, Denmark) in the volume 100 µl/pit. After sticking of cells (24 hours) the liquid was carefully pulled down and then different concentrations of AKG and examined cytostatics (cyclophosphamide, iphosphamid, thiotepa) in liquid with 10% FBS (100 ∥l/pit) were added. The cultures on plates were left for 96 hours incubation at a temperature of 37° C., in the atmosphere 95% air and 5% $CO_2$. The antiproliferative activity of examined substances was assessed with the method MTT.

The Method MTT (According to Kit "Cell Proliferation Kit III", Boehringer Manheim)

This method was worked out to determine the proliferation and vitality of cells in studies on the cytotoxic and antiproliferative substances. In metabolically active cells tetrazolic yellow salt MTT is reduced to formazane blue with the mitochondrial dehydrases. Formazane crystals, insoluble in water, accumulate in cells and for their dissolutions the use of organic detergent, breaking the membrane and simultaneously solvent the dye, is necessary. For this purpose the buffer SDS-HCl with pH 7.4 is used. The concentration of released dye is evaluated quantitatively in the reader for 96-pits plates at the wavelength 570 nm. The colour intensity is directly proportional to the quantity of alive cells.

MTT solution in PBS condition in concentration 5 mg/ml was added into each pit on a plastic plate in a dose of 15 μl/pit. Plates were incubated for 3 hours at a temperature of 37° C. Thereafter, buffer SDS-HCl in a does 100 μl/pit was added and the plates were left at a temperature of 37° C. all night. The results were evaluated next day with the use of E-max Reader (Molecular Devices Corporation, Menlo Park, Calif., U.S.A.).

Evaluation of Cells Migration Degree with the Method "Wound Assay"

This method is for the estimation of the activity of substances affecting the mobility of cells in vitro. It is used in research on wounds healing, angiogenesis and neoplastic metastases.

C6 cells ($1 \times 10^6$) suspended in the culture basis with the addition of 10% serum (FBS) were poured onto the culture plates (NUNC, Roskilde, Denmark) with 4 cm diameter. Next day in the equal layer of cells the flaw (wound) was done with the ending of automatic pipette and unstuck cells were removed by twice-rinsing the plates with a PBS solution. Then, AKG (10 and 20 mM) dissolved in the culture basis was added to the prepared culture. Plates were incubated for 24 hours in a temperature of 37° C. and in a humid atmosphere 95% air and 5% $CO_2$. Thereafter the cultures were coloured with the May-Grünwald-Giemza method. Then the microscopic analysis was performed with the microscope Olympus BX51 (Olympus Optical CO., LTD, Tokyo, Japan) with the use of the software analySIS® (Soft Imaging System GmbH, Münster, Germany). The degree of cells migration was assessed in cytometry as the number of cells which populated the wound done earlier in the layer of cells. At least 50 chosen fields on 8 photographs were assessed.

Results: The Estimation of Antiproliferative Activity of AKG

Antiproliferative activity of AKG in the cultures was estimated in differen kinds of neoplastic cells: the lung cancer cells (A549), the large intestine cancer cells (HT-29) and glioma cells (C6). Cells were processed with AKG in concentrations 0.5, 1, 2.5, 5, 10 and 20 mM, for 96 hours.

Figure 2:
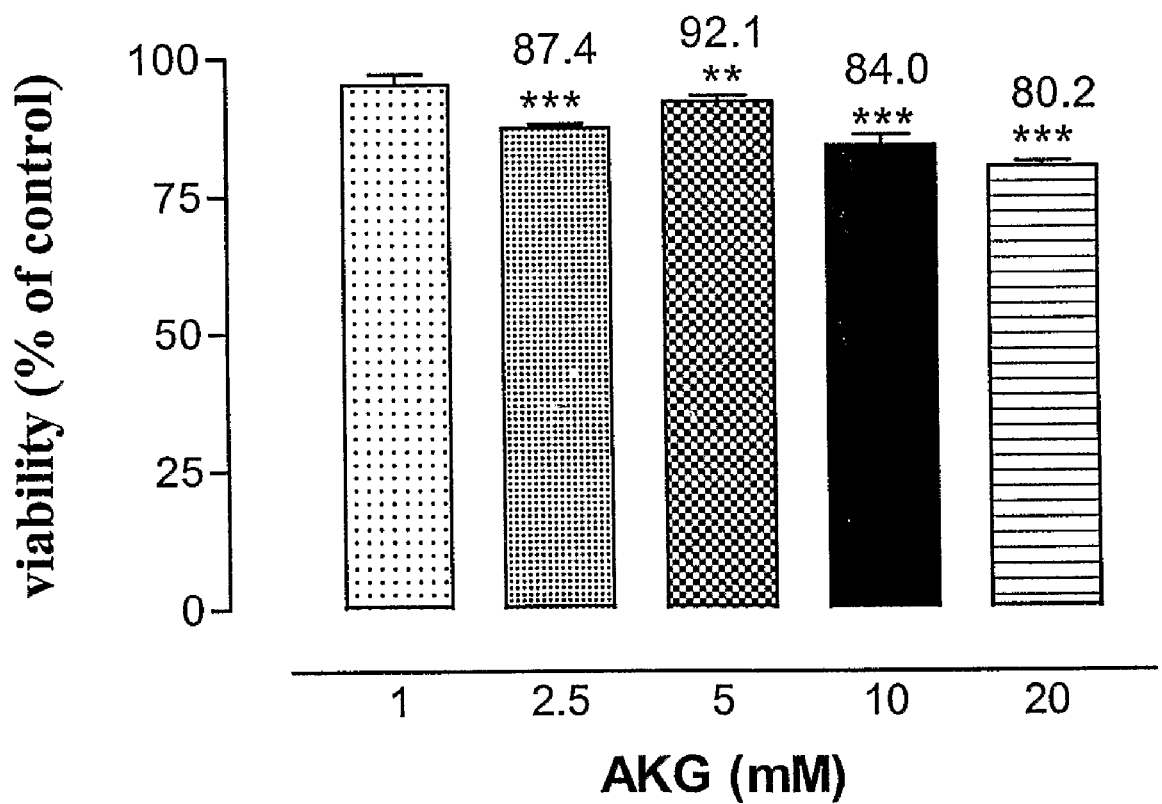
FIG. 2 depicts the proliferation of C6 cells with AKG.
Figure 3:
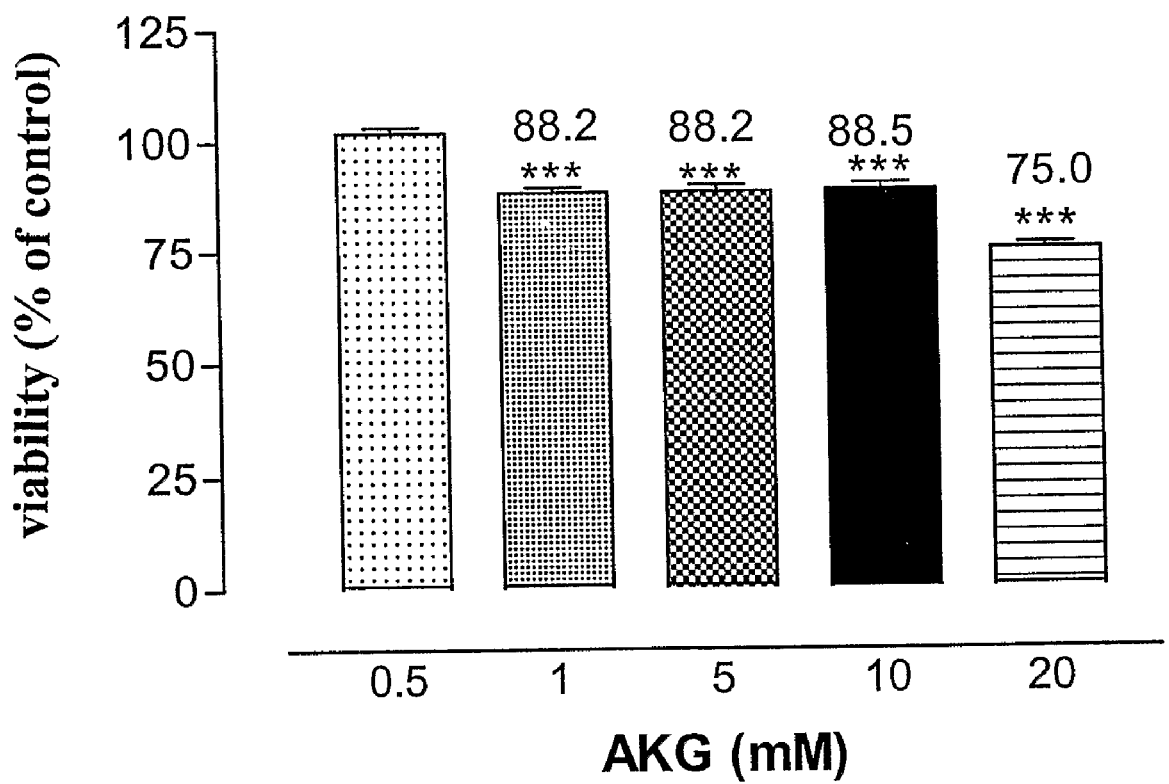
FIG. 3 depicts the proliferation of HT-29 cells with AKG stimulation.

The examined substance has had antiproliferative activity with relation to all neoplastic cells types (see the diagram—FIG. 1, FIG. 2, FIG. 3). Statistically significant (4.5%) inhibition of cells' growth was observed at AKG concentration 2.5 mM in A549 cell line in the comparison to the control group. That effect was correlated with a dose of AKG and was 7.8%, 12.4%, 17.5% with doses 5 mM, 10 mM and 20 mM respectively (see the diagram on FIG. 1). The growth inhibition in glioma cells (C6) was 12.6% with AKG dose 2.5 mM, 7.9%—5 mM, 16%—10 mM and 19.8%—20 mM, respectively. The growth inhibition of large intestine cancer cells (HT-29) hadn't had the lineal character with AKG concentrations between 1 and 10 mM. The dose 1 mM inhibited the cells growth by 11.8%. The similar effect was obtained with a dose 5 mM (11.8%) and 10 mM (11.5%). Only a dose 20 mM caused the significant (25%) inhibition of these cells' growth (the diagram—FIG. 3).

The Estimation of the Interaction Between AKG and Antineoplastic Drugs

Figure 4:
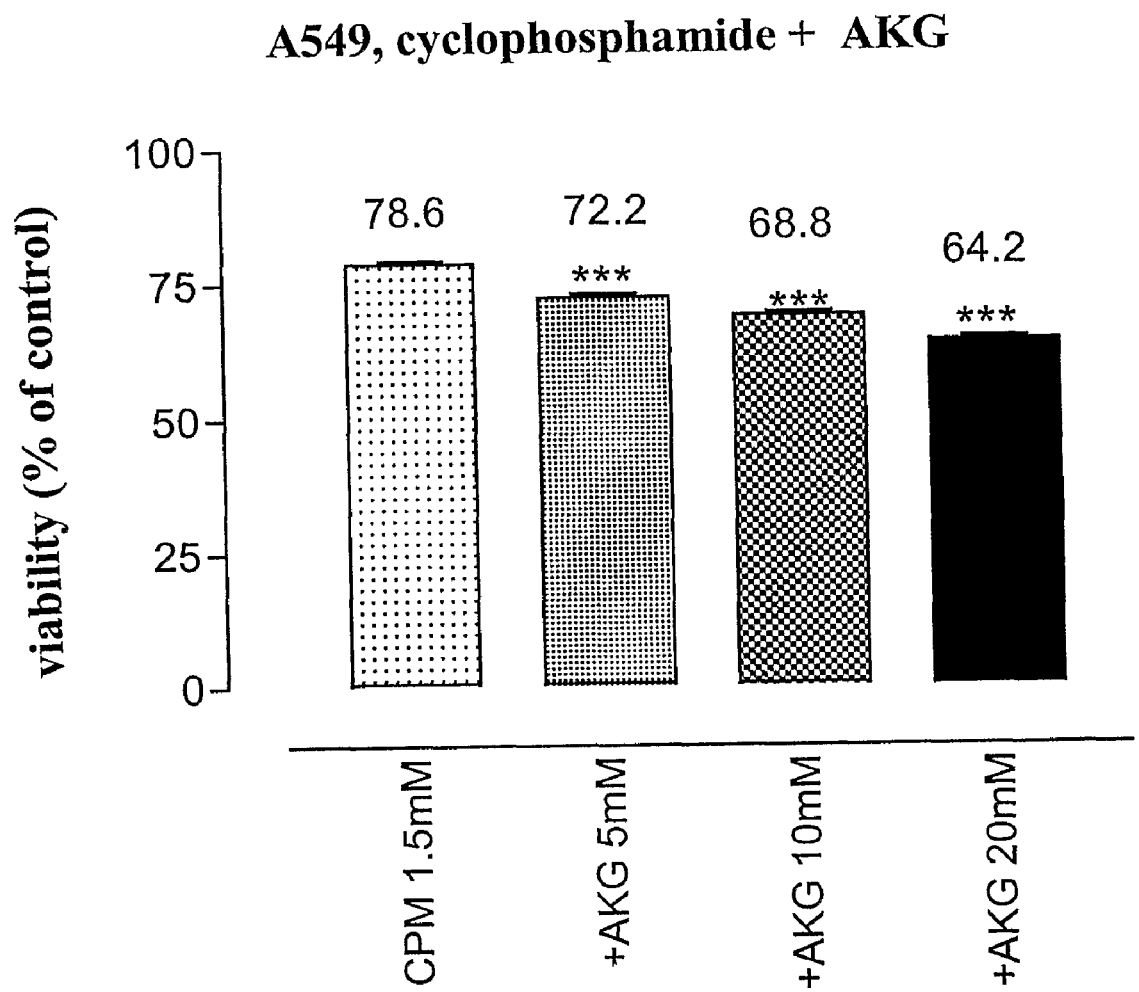
FIG. 4 presents the proliferation of human neoplastic cells A549 in the presence of the cyclophosphamide with AKG.
Figure 5:
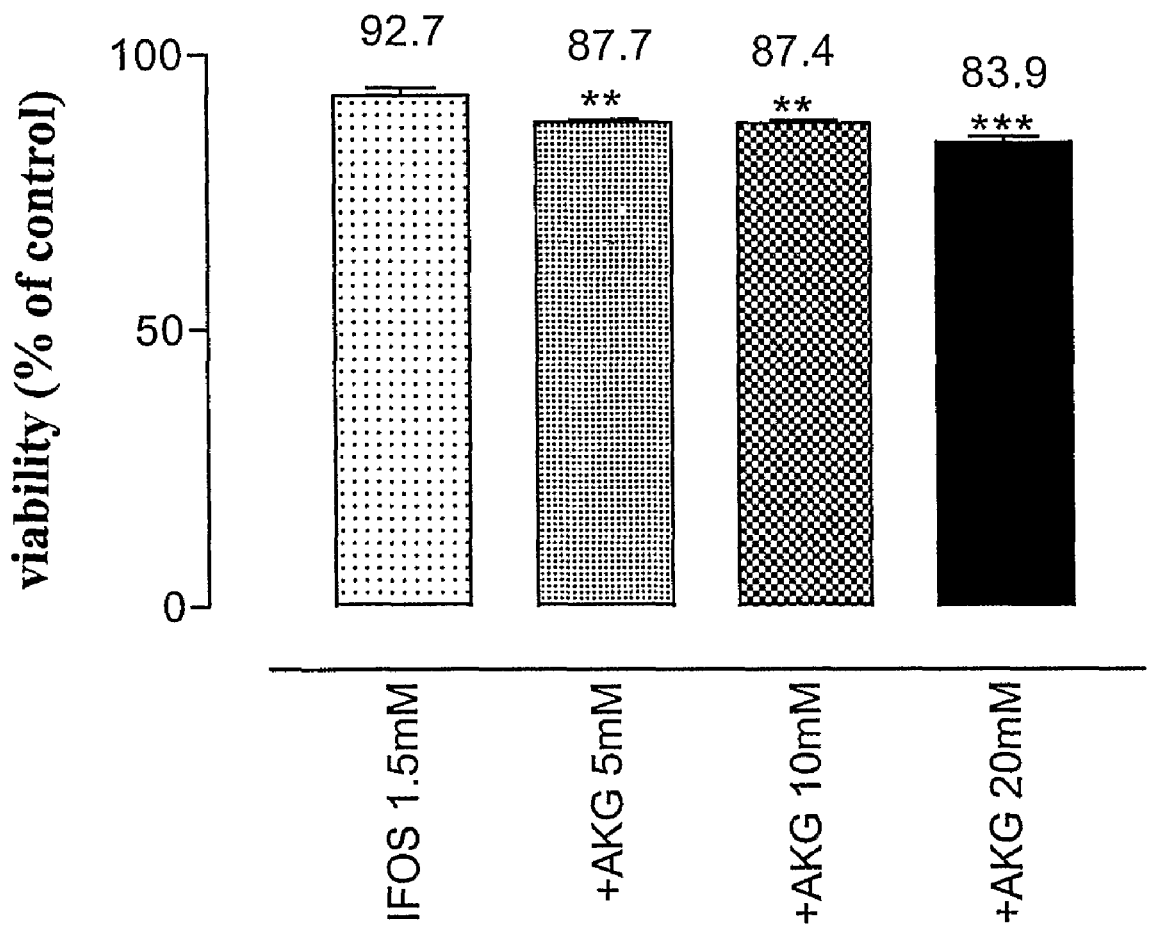
FIG. 5 depicts the proliferation of human neoplastic cells A549 in the presence of iphosphamide with AKG.
Figure 6:
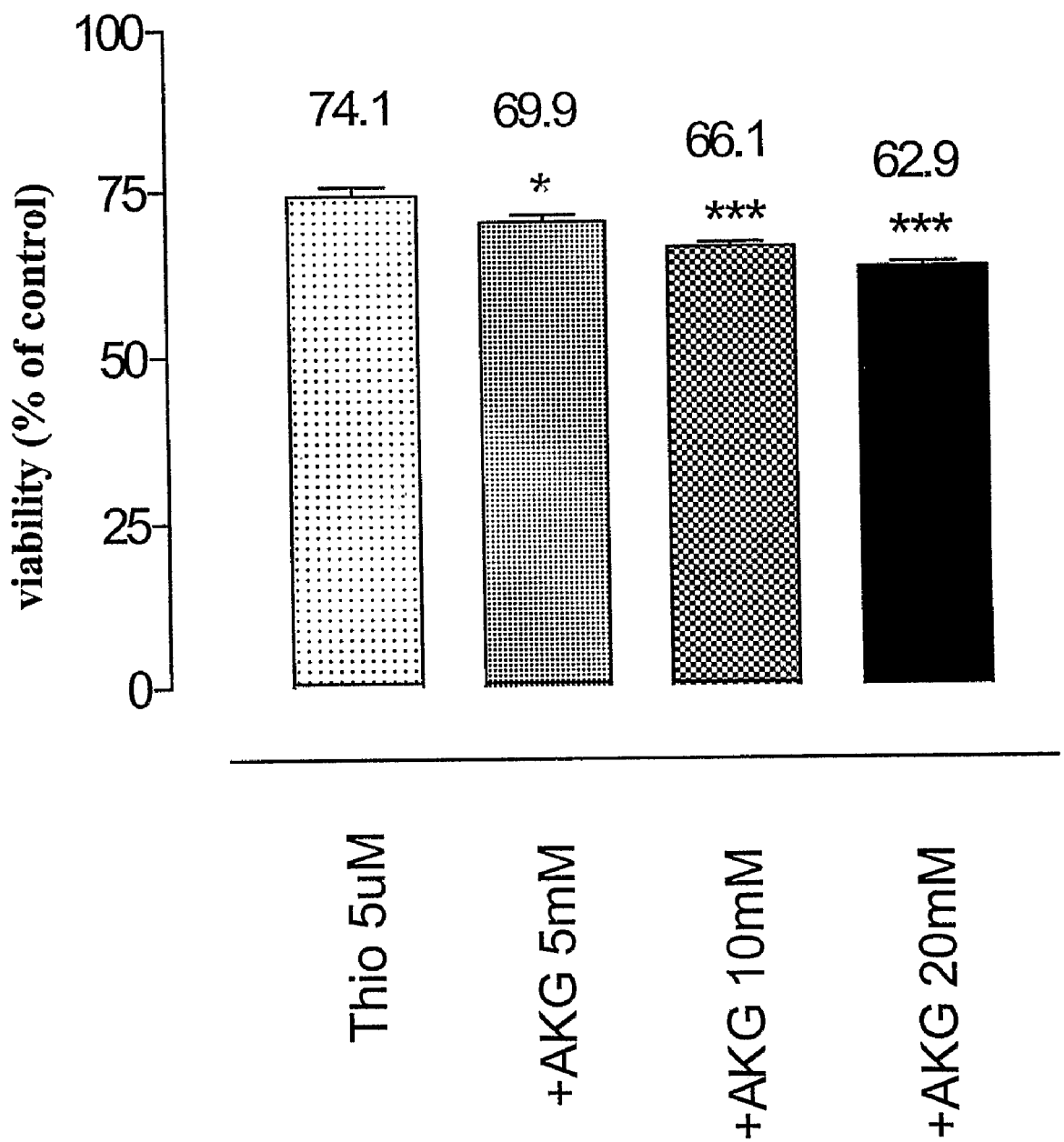
FIG. 6 depicts the proliferation of human neoplastic cells A549 in the presence of thiotepa with AKG.

The research on the interaction between AKG and popular cytostatics used in cancer chemotherapy was performed in the culture of lung cancer cells (A549). For that purpose cells were treated with the following cytostatics: cyclophosphamide (1.5 mM), iphosphamid (1.5 mM) and thiotepa (5 μM), alone and in combination with AKG (5, 10 and 20 mM). The additive effect of AKG on cytostatic activity of used chemotherapeutics was observed (results are presented on FIG. 4, FIG. 5 and FIG. 6). Cyclophosphamide in a concentration 1.5 mM inhibited the growth of A549 cells by 21.4%. The addition of AKG increased its cytostatic activity by 6.4%, 9.8% and 14.4% respectively (the diagram—FIG. 4). Iphosphamid (1.5 mM) inhibited the cells growth by 7.3%. After AKG addition (5, 10 and 20 mM) that effect increased by 5%, 5.3% and 8.8% respectively (the diagram—FIG. 5). AKG intensified also cytostatic activity of thiotepa (5 μM—25.9%) by 4.2% (5 mM), 8% (10 mM) and 11.2% (20 mM) (results are presented on FIG. 6).

The Influence of AKG on the Migration of Neoplastic Cells

Figure 7:
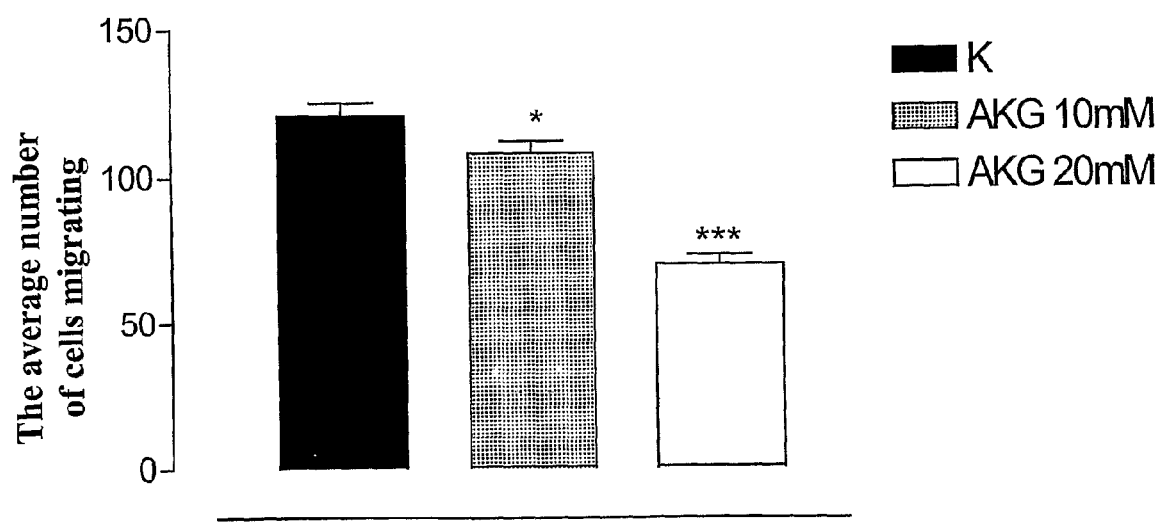
FIG. 7 depicts the inhibition of C6 cells migration due to AKG.

The research on the mobility of neoplastic cells was passed in the "wound assay" model. At the photograph 1 the wound in the layer of C6 cells (A), the wound population with cells after 24 hours of incubation without AKG (B) and significant inhibition of cells migration in the presence of AKG 20 mM (C) are presented. On the diagram—FIG. 7, the average number of cells migrating to one field of flaw done in the uniform layer of cells is presented. Statistically significant inhibition of cells migration in the presence of 10 mM and 20 mM AKG was shown.

The Statistical Analysis

The statistical analysis was performed with the use of t-student test. * $p<0.05$,  $p<0.01$, * $p<0.001$.

The invention claimed is:

1. A method for treatment of neoplastic diseases, comprising:
    administering an antineoplastic preparation wherein the active component consists of alpha-ketoglutarate and/or mono- or divalent metal salts of alpha-ketoglutarate to a subject in need thereof,
    wherein the neoplastic disease is selected from the group consisting of cancer of the lung, glioma, and cancer of the large intestine.

* * * * *